(12) United States Patent
Tarasova et al.

(10) Patent No.: US 9,056,891 B2
(45) Date of Patent: Jun. 16, 2015

(54) SYNTHETIC PEPTIDE INHIBITORS OF WNT PATHWAY

(71) Applicant: The United States of America, as represented by the Secretary, Department of Health and Human Services, Washington, DC (US)

(72) Inventors: Nadya I. Tarasova, Frederick, MD (US); Alan O. Perantoni, Fairfield, PA (US); Shunsuke Tanigawa, Frederick, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 13/917,958

(22) Filed: Jun. 14, 2013

(65) Prior Publication Data

US 2013/0273058 A1 Oct. 17, 2013

Related U.S. Application Data

(63) Continuation-in-part of application No. PCT/US2011/064902, filed on Dec. 14, 2011.

(60) Provisional application No. 61/422,857, filed on Dec. 14, 2010.

(51) Int. Cl.
*C07K 7/00* (2006.01)
*C07K 7/08* (2006.01)
*C07K 14/47* (2006.01)
*A61K 38/00* (2006.01)

(52) U.S. Cl.
CPC .............. *C07K 7/08* (2013.01); *C07K 14/4703* (2013.01); *A61K 38/00* (2013.01)

(58) Field of Classification Search
None
See application file for complete search history.

(56) References Cited

U.S. PATENT DOCUMENTS

| 6,303,576 B1 | 10/2001 | Blaschuk et al. |
| 6,551,994 B1 | 4/2003 | Blaschuk et al. |
| 6,706,685 B1 | 3/2004 | Blaschuk et al. |
| 7,067,474 B1 | 6/2006 | Birchmeier et al. |

OTHER PUBLICATIONS

European Patent Office, International Search Report in International Patent Application No. PCT/US2011/064902 (Jun. 1, 2012).
European Patent Office, Written Opinion in International Patent Application No. PCT/US2011/064902 (Jun. 1, 2012).
Mo et al., "The terminal region of β-catenin promotes stability by shielding the armadillo repeats from the axin-scaffold destruction complex," *Journal of Biological Chemistry*, 284(41): 28222-28231 (2009).
OMIM Database, "Beta-Catenin," Database Accession No. 116806, retrieved from http://omim.org/entry/116806, pp. 1-42, (2012).
Tanigawa et al., "Wnt4 induces nephronic tubules in metanephric mesenchyme by a non-canonical mechanism," *Developmental Biology*, 352(1): 58-69 (2011).
Tutter et al., "Chromatin-specific regulation of LEF-1-β-catenin transcription activation and inhibition in vitro," *Genes & Development*, 15: 3342-3354 (2001).
Xing et al., "Crystal structure of a full-length β-catenin," *Structure*, 16(3): 478-487 (2008).

*Primary Examiner* — Sheela J Huff
(74) *Attorney, Agent, or Firm* — Leydig, Voit & Mayer, Ltd.

(57) ABSTRACT

A peptide or peptidomimetic comprising the amino acid sequence KKRLSVXLTSSLFR (SEQ ID NO: 1) or the inverse thereof, or comprising at least eight contiguous amino acids of helix C of β-catenin (SEQ ID NO: 41) or inverse thereof, wherein the peptide or peptidomimetic comprises a total of about 50 or fewer amino acids and inhibits the Wnt pathway, as well as a method of inhibiting the Wnt pathway in a cell, a method of treating or preventing a disease mediated by the Wnt pathway, and related compounds, compositions, and methods.

23 Claims, 4 Drawing Sheets

SEQUENCE LISTING

```
<160> NUMBER OF SEQ ID NOS: 49

<210> SEQ ID NO 1
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 1

Lys Lys Arg Leu Ser Val Xaa Leu Thr Ser Ser Leu Phe Arg
1               5                   10

<210> SEQ ID NO 2
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 2

Xaa Lys Lys Arg Leu Ser Val Xaa Leu Thr Ser Ser Leu Phe Arg
1               5                   10                  15

<210> SEQ ID NO 3
<211> LENGTH: 16
<212> TYPE: PRT
<213> ORGANISM: Artificial Sequence
<220> FEATURE:
```

```
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid

<400> SEQUENCE: 3

Xaa Lys Lys Arg Leu Ser Val Xaa Leu Thr Ser Ser Leu Phe Arg Xaa
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 4

Lys Lys Arg Leu Ser Val Xaa Leu Thr Ser Ser Leu Phe Arg Xaa
1               5                   10                  15

<210> SEQ ID NO 5
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (15)..(16)
<223> OTHER INFORMATION: Xaa can be any naturally occurring amino acid

<400> SEQUENCE: 5

Lys Lys Arg Leu Ser Val Xaa Leu Thr Ser Ser Leu Phe Arg Xaa Xaa
1               5                   10                  15

<210> SEQ ID NO 6
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (16)..(17)
```

-continued

<223> OTHER INFORMATION: Xaa can be any naturally occurring amino acid

<400> SEQUENCE: 6

Xaa Lys Lys Arg Leu Ser Val Xaa Leu Thr Ser Ser Leu Phe Arg Xaa
1               5                   10                  15

Xaa

<210> SEQ ID NO 7
<211> LENGTH: 14
<212> TYPE: PRT
<213> ORGANISM: Artificial Sequence
<220> FEATURE:
<223> OTHER INFORMATION: Synthetic

<400> SEQUENCE: 7

Lys Lys Arg Leu Ser Val Glu Leu Thr Ser Ser Leu Phe Arg
1               5                   10

<210> SEQ ID NO 8
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid

<400> SEQUENCE: 8

Xaa Lys Lys Arg Leu Ser Val Glu Leu Thr Ser Ser Leu Phe Arg
1               5                   10                  15

<210> SEQ ID NO 9
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid

<400> SEQUENCE: 9

Xaa Lys Lys Arg Leu Ser Val Glu Leu Thr Ser Ser Leu Phe Arg Xaa
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (15)..(15)
<223> OTHER INFORMATION: Xaa can be any naturally occurring amino acid

<400> SEQUENCE: 10

Lys Lys Arg Leu Ser Val Glu Leu Thr Ser Ser Leu Phe Arg Xaa
1               5                   10                  15

<210> SEQ ID NO 11

```
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (15)..(16)
<223> OTHER INFORMATION: Xaa can be any naturally occurring amino acid

<400> SEQUENCE: 11

Lys Lys Arg Leu Ser Val Glu Leu Thr Ser Ser Leu Phe Arg Xaa Xaa
1               5                   10                  15

<210> SEQ ID NO 12
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (16)..(17)
<223> OTHER INFORMATION: Xaa can be any naturally occurring amino acid

<400> SEQUENCE: 12

Xaa Lys Lys Arg Leu Ser Val Glu Leu Thr Ser Ser Leu Phe Arg Xaa
1               5                   10                  15

Xaa

<210> SEQ ID NO 13
<211> LENGTH: 14
<212> TYPE: PRT
<213> ORGANISM: Artificial Sequence
<220> FEATURE:
<223> OTHER INFORMATION: Synthetic

<400> SEQUENCE: 13

Lys Lys Arg Leu Ser Val Gln Leu Thr Ser Ser Leu Phe Arg
1               5                   10

<210> SEQ ID NO 14
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid

<400> SEQUENCE: 14

Xaa Lys Lys Arg Leu Ser Val Gln Leu Thr Ser Ser Leu Phe Arg
1               5                   10                  15

<210> SEQ ID NO 15
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
```

```
<220> FEATURE:
<221> NAME/KEY: misc_feature
<222> LOCATION: (16)..(16)
<223> OTHER INFORMATION: Xaa can be any naturally occurring amino acid

<400> SEQUENCE: 15

Xaa Lys Lys Arg Leu Ser Val Gln Leu Thr Ser Ser Leu Phe Arg Xaa
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (15)..(15)
<223> OTHER INFORMATION: Xaa can be any naturally occurring amino acid

<400> SEQUENCE: 16

Lys Lys Arg Leu Ser Val Gln Leu Thr Ser Ser Leu Phe Arg Xaa
1               5                   10                  15

<210> SEQ ID NO 17
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (15)..(16)
<223> OTHER INFORMATION: Xaa can be any naturally occurring amino acid

<400> SEQUENCE: 17

Lys Lys Arg Leu Ser Val Gln Leu Thr Ser Ser Leu Phe Arg Xaa Xaa
1               5                   10                  15

<210> SEQ ID NO 18
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (16)..(17)
<223> OTHER INFORMATION: Xaa can be any naturally occurring amino acid

<400> SEQUENCE: 18

Xaa Lys Lys Arg Leu Ser Val Gln Leu Thr Ser Ser Leu Phe Arg Xaa
1               5                   10                  15

Xaa

<210> SEQ ID NO 19
<211> LENGTH: 60
<212> TYPE: PRT
<213> ORGANISM: Mus musculus

<400> SEQUENCE: 19

Glu Ala Ile Glu Ala Glu Gly Ala Thr Ala Pro Leu Thr Glu Leu Leu
1               5                   10                  15

His Ser Arg Asn Glu Gly Val Ala Thr Tyr Ala Ala Ala Val Leu Phe
```

```
                    20                  25                  30

Arg Met Ser Glu Asp Lys Pro Gln Asp Tyr Lys Lys Arg Leu Ser Val
            35                  40                  45

Glu Leu Thr Ser Ser Leu Phe Arg Thr Glu Pro Met
        50                  55                  60

<210> SEQ ID NO 20
<211> LENGTH: 60
<212> TYPE: PRT
<213> ORGANISM: Rattus norvegicus

<400> SEQUENCE: 20

Glu Ala Ile Glu Ala Glu Gly Ala Thr Ala Pro Leu Thr Glu Leu Leu
1               5                   10                  15

His Ser Arg Asn Glu Gly Val Ala Thr Tyr Ala Ala Ala Val Leu Phe
                20                  25                  30

Arg Met Ser Glu Asp Lys Pro Gln Asp Tyr Lys Lys Arg Leu Ser Val
            35                  40                  45

Glu Leu Thr Ser Ser Leu Phe Arg Thr Glu Pro Met
        50                  55                  60

<210> SEQ ID NO 21
<211> LENGTH: 60
<212> TYPE: PRT
<213> ORGANISM: Homo sapiens

<400> SEQUENCE: 21

Glu Ala Ile Glu Ala Glu Gly Ala Thr Ala Pro Leu Thr Glu Leu Leu
1               5                   10                  15

His Ser Arg Asn Glu Gly Val Ala Thr Tyr Ala Ala Ala Val Leu Phe
                20                  25                  30

Arg Met Ser Glu Asp Lys Pro Gln Asp Tyr Lys Lys Arg Leu Ser Val
            35                  40                  45

Glu Leu Thr Ser Ser Leu Phe Arg Thr Glu Pro Met
        50                  55                  60

<210> SEQ ID NO 22
<211> LENGTH: 60
<212> TYPE: PRT
<213> ORGANISM: Bos taurus

<400> SEQUENCE: 22

Glu Ala Ile Glu Ala Glu Gly Ala Thr Ala Pro Leu Thr Glu Leu Leu
1               5                   10                  15

His Ser Arg Asn Glu Gly Val Ala Thr Tyr Ala Ala Ala Val Leu Phe
                20                  25                  30

Arg Met Ser Glu Asp Lys Pro Gln Asp Tyr Lys Lys Arg Leu Ser Val
            35                  40                  45

Glu Leu Thr Ser Ser Leu Phe Arg Thr Glu Pro Met
        50                  55                  60

<210> SEQ ID NO 23
<211> LENGTH: 60
<212> TYPE: PRT
<213> ORGANISM: Xenopus

<400> SEQUENCE: 23

Glu Ala Ile Glu Ala Glu Gly Ala Thr Ala Pro Leu Thr Glu Leu Leu
1               5                   10                  15
```

His Ser Arg Asn Glu Gly Val Ala Thr Tyr Ala Ala Val Leu Phe
            20                  25                  30

Arg Met Ser Glu Asp Lys Pro Gln Asp Tyr Lys Lys Arg Leu Ser Val
        35                  40                  45

Glu Leu Thr Ser Ser Leu Phe Arg Thr Glu Pro Met
    50                  55                  60

<210> SEQ ID NO 24
<211> LENGTH: 60
<212> TYPE: PRT
<213> ORGANISM: Danio rerio

<400> SEQUENCE: 24

Glu Ala Ile Glu Ala Glu Gly Ala Thr Ala Pro Leu Thr Glu Leu Leu
1               5                   10                  15

His Ser Arg Asn Glu Gly Val Ala Thr Tyr Ala Ala Val Leu Phe
            20                  25                  30

Arg Met Ser Glu Asp Lys Pro Gln Asp Tyr Lys Lys Arg Leu Ser Val
        35                  40                  45

Glu Leu Thr Ser Ser Leu Phe Arg Thr Glu Pro Met
    50                  55                  60

<210> SEQ ID NO 25
<211> LENGTH: 60
<212> TYPE: PRT
<213> ORGANISM: Echinoidea

<400> SEQUENCE: 25

Glu Met Ile Glu Gln Gly Gly Ala Thr Ala Pro Leu Thr Glu Leu Leu
1               5                   10                  15

His Ser Arg Asn Glu Gly Val Ala Thr Tyr Ala Ala Val Leu Tyr
            20                  25                  30

Arg Met Ser Asp Asp Lys Pro Gln Asp Tyr Lys Lys Arg Ile Ser Val
        35                  40                  45

Glu Leu Gly Asn Ser Leu Phe Arg Gly Asp Ser Val
    50                  55                  60

<210> SEQ ID NO 26
<211> LENGTH: 60
<212> TYPE: PRT
<213> ORGANISM: Echiura

<400> SEQUENCE: 26

Glu Met Ile Glu Gln Glu Gly Thr Thr Ala Pro Leu Thr Glu Leu Leu
1               5                   10                  15

His Ser Arg Asn Glu Gly Val Ala Thr Tyr Ala Ala Val Leu Phe
            20                  25                  30

Arg Met Ser Glu Asp Lys Pro Gln Asp Tyr Lys Lys Arg Leu Ser Val
        35                  40                  45

Glu Leu Thr Ser Ser Leu Phe Arg Gly Glu Gln Val
    50                  55                  60

<210> SEQ ID NO 27
<211> LENGTH: 60
<212> TYPE: PRT
<213> ORGANISM: Drosophila

<400> SEQUENCE: 27

Glu Ile Ile Glu Gln Glu Gly Ala Thr Gly Pro Leu Thr Asp Leu Leu
1               5                   10                  15

His Ser Arg Asn Glu Gly Val Ala Thr Tyr Ala Ala Ala Val Leu Phe
            20                  25                  30

Arg Met Ser Glu Asp Lys Pro Gln Asp Tyr Lys Lys Arg Leu Ser Ile
        35                  40                  45

Glu Leu Thr Asn Ser Leu Leu Arg Glu Asp Asn Asn
    50                  55                  60

<210> SEQ ID NO 28
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is palmitoylated lysine

<400> SEQUENCE: 28

Xaa Tyr Lys Lys Arg Leu Ser Val Glu Leu Thr Ser Ser Leu Phe Arg
1               5                   10                  15

<210> SEQ ID NO 29
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is palmitoylated proline

<400> SEQUENCE: 29

Xaa Gln Asn Tyr Lys Lys Arg Leu Ser Val Glu Leu Thr Ser Ser Leu
1               5                   10                  15

Phe Arg

<210> SEQ ID NO 30
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is palmitoylated tyrosine

<400> SEQUENCE: 30

Xaa Lys Lys Arg Leu Ser Val Glu Leu Thr Ser Ser Leu Phe Arg
1               5                   10                  15

<210> SEQ ID NO 31
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is palmitoylated lysine

<400> SEQUENCE: 31

Xaa Gln Asp Tyr Lys Lys Arg Leu Ser Val Glu Leu Thr Ser Ser Leu
1               5                   10                  15

Phe Arg

<210> SEQ ID NO 32
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is palmitoylated lysine

<400> SEQUENCE: 32

Xaa Tyr Lys Lys Arg Leu Ser Val Gln Leu Thr Ser Ser Leu Phe Arg
1               5                   10                  15

<210> SEQ ID NO 33
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is 2-dodecyl-alanine

<400> SEQUENCE: 33

Xaa Tyr Lys Lys Arg Leu Ser Val Glu Leu Thr Ser Ser Leu Phe Arg
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is acetylated tyrosine
<220> FEATURE:
<221> NAME/KEY: MISC_FEATURE
<222> LOCATION: (7)..(7)
<223> OTHER INFORMATION: Xaa is 2-(4'-pentenyl)alanine
<220> FEATURE:
<221> NAME/KEY: MISC_FEATURE
<222> LOCATION: (11)..(11)
<223> OTHER INFORMATION: Xaa is 2-(4'-pentenyl)alanine

<400> SEQUENCE: 34

Xaa Lys Lys Arg Leu Ser Xaa Glu Leu Thr Xaa Ser Leu Phe Arg
1               5                   10                  15

<210> SEQ ID NO 35
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is acetylated arginine
<220> FEATURE:
<221> NAME/KEY: MISC_FEATURE
<222> LOCATION: (16)..(16)
<223> OTHER INFORMATION: Xaa is palmitoylated lysine

<400> SEQUENCE: 35

Xaa Phe Leu Ser Ser Thr Leu Glu Val Ser Leu Arg Lys Lys Tyr Xaa
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is palmitoylated threonine
<220> FEATURE:
<221> NAME/KEY: MISC_FEATURE
<222> LOCATION: (15)..(15)
<223> OTHER INFORMATION: Xaa is amidated lysine

<400> SEQUENCE: 36

Xaa Arg Phe Leu Ser Ser Thr Leu Glu Val Ser Leu Arg Lys Xaa
1               5                   10                  15

<210> SEQ ID NO 37
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is palmitoylated threonine
<220> FEATURE:
<221> NAME/KEY: MISC_FEATURE
<222> LOCATION: (16)..(16)
<223> OTHER INFORMATION: Xaa is amidated tyrosine

<400> SEQUENCE: 37

Xaa Arg Phe Leu Ser Ser Thr Leu Glu Val Ser Leu Arg Lys Lys Xaa
1               5                   10                  15

<210> SEQ ID NO 38
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is palmitoylated amino-isobutyric acid
<220> FEATURE:
<221> NAME/KEY: MISC_FEATURE
<222> LOCATION: (16)..(16)
<223> OTHER INFORMATION: Xaa is amidated tyrosine

<400> SEQUENCE: 38

Xaa Arg Phe Leu Ser Ser Thr Leu Glu Val Ser Leu Arg Lys Lys Xaa
1               5                   10                  15

<210> SEQ ID NO 39
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is palmitoylated lysine
<220> FEATURE:

```
<221> NAME/KEY: MISC_FEATURE
<222> LOCATION: (16)..(16)
<223> OTHER INFORMATION: Xaa is amidated lysine

<400> SEQUENCE: 39

Xaa Thr Arg Phe Leu Ser Ser Thr Leu Glu Val Ser Leu Arg Lys Xaa
1               5                   10                  15

<210> SEQ ID NO 40
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: Xaa can be any naturally occurring amino acid

<400> SEQUENCE: 40

Xaa Xaa Xaa Tyr Lys Lys Arg Leu Ser Val Glu Leu Thr Ser Ser Leu
1               5                   10                  15

Phe Arg

<210> SEQ ID NO 41
<211> LENGTH: 17
<212> TYPE: PRT
<213> ORGANISM: Artificial Sequence
<220> FEATURE:
<223> OTHER INFORMATION: Synthetic

<400> SEQUENCE: 41

Gln Asp Tyr Lys Lys Arg Leu Ser Val Glu Leu Thr Ser Ser Leu Phe
1               5                   10                  15

Arg

<210> SEQ ID NO 42
<211> LENGTH: 37
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(23)
<223> OTHER INFORMATION: Xaa is any amino acid

<400> SEQUENCE: 42

Ala Ala Ala Val Leu Phe Arg Met Ser Glu Asp Lys Pro Gln Asp Tyr
1               5                   10                  15

Lys Lys Arg Leu Ser Val Xaa Leu Thr Ser Ser Leu Phe Arg Thr Glu
            20                  25                  30

Pro Met Ala Trp Asn
            35

<210> SEQ ID NO 43
<211> LENGTH: 21
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is palmitoylated tyrosine

<400> SEQUENCE: 43
```

```
Xaa Lys Lys Arg Leu Ser Val Glu Leu Thr Ser Ser Leu Phe Arg Thr
1               5                   10                  15

Glu Pro Met Ala Trp
            20

<210> SEQ ID NO 44
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is palmitoylated amino-isobutyric acid

<400> SEQUENCE: 44

Xaa Tyr Lys Lys Arg Leu Ser Val Glu Leu Thr Ser Ser Leu Phe Arg
1               5                   10                  15

<210> SEQ ID NO 45
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is palmitoylated amino-isobutyric acid

<400> SEQUENCE: 45

Xaa Tyr Lys Lys Arg Leu Ser Val Gln Leu Thr Ser Ser Leu Phe Arg
1               5                   10                  15

<210> SEQ ID NO 46
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is palmitoylated threonine
<220> FEATURE:
<221> NAME/KEY: MISC_FEATURE
<222> LOCATION: (15)..(15)
<223> OTHER INFORMATION: Xaa is amidated lysine

<400> SEQUENCE: 46

Xaa Arg Phe Leu Ser Ser Thr Leu Gln Val Ser Leu Arg Lys Xaa
1               5                   10                  15

<210> SEQ ID NO 47
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is palmitoylated arginine
<220> FEATURE:
<221> NAME/KEY: MISC_FEATURE
<222> LOCATION: (14)..(14)
<223> OTHER INFORMATION: Xaa is amidated lysine

<400> SEQUENCE: 47
```

```
Xaa Phe Leu Ser Ser Thr Leu Gln Val Ser Leu Arg Lys Xaa
1               5                   10

<210> SEQ ID NO 48
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is capric acid-linked threonine
<220> FEATURE:
<221> NAME/KEY: MISC_FEATURE
<222> LOCATION: (15)..(15)
<223> OTHER INFORMATION: Xaa is amidated lysine

<400> SEQUENCE: 48

Xaa Arg Phe Leu Ser Ser Thr Leu Gln Val Ser Leu Arg Lys Xaa
1               5                   10                  15

<210> SEQ ID NO 49
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is lauric acid-linked threonine
<220> FEATURE:
<221> NAME/KEY: MISC_FEATURE
<222> LOCATION: (15)..(15)
<223> OTHER INFORMATION: Xaa is amidated lysine

<400> SEQUENCE: 49

Xaa Arg Phe Leu Ser Ser Thr Leu Gln Val Ser Leu Arg Lys Xaa
1               5                   10                  15
```

SYNTHETIC PEPTIDE INHIBITORS OF WNT PATHWAY

CROSS-REFERENCE TO RELATED APPLICATIONS

This patent application is a continuation-in-part of PCT/US11/64902, filed Dec. 14, 2011, which claims the benefit of U.S. Provisional Patent Application No. 61/422,857, filed Dec. 14, 2010, which applications are hereby incorporated by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 20,948 Byte ASCII (Text) file named "713694ST25.TXT," created on Jun. 10, 2013.

BACKGROUND OF THE INVENTION

The Wnt pathway has an established role in human neoplasms, such as the pediatric renal cancer called Wilms' tumor, colorectal cancer, pancreatic cancer, lung cancer, prostate cancer, leukemia, and other cancers. Additionally, aberrations in the Wnt pathway have been reported to be involved in metastasis of cancer (e.g., prostate cancer), especially to bone.

The Wnt pathway has many members and interacts with a variety of signaling pathways. For example, the Disheveled (Dvl) family proteins (Dsh in Drosophila) are membrane-proximal signaling intermediates in the Wnt pathway. Downstream of Dvl is the enzyme GSK3β, a serine-threonine kinase that is a negative regulator of insulin and Wnt signaling. In the absence of a Wnt signal, GSK3β phosphorylates β-catenin and induces its ubiquitination and proteolytic degradation. The presence of a Wnt signal inhibits GSK3β, which stabilizes β-catenin, allowing it to translocate to the nucleus, where it acts as an essential cofactor for Tcf/Lef-dependent transcription. β-catenin-Tcf/Lef induces transcription of important downstream target genes, such as c-myc and cyclin D1, many of which have been implicated in cancer.

Additionally, adenomatous polyposis coli (APC) tumor suppressor gene, which is mutated in about 80% of sporadic colorectal cancers, interacts with β-catenin. Mutations in APC lead to uncontrolled activation of β-catenin leading to cancer. Thus, Wnt signaling results in β-catenin accumulation and transcriptional activation of specific target genes that are normally activated during development and aberrantly activated during cancer.

Therefore, there is a desire to identify new antagonists of the Wnt pathway in order to investigate those interactions, as well as to provide more effective chemotherapies for tumors that depend upon Wnt signaling.

BRIEF SUMMARY OF THE INVENTION

The invention provides a peptide or peptidomimetic comprising the amino acid sequence KKRLSVXLTSSLFR (SEQ ID NO: 1) or the inverse thereof, wherein the peptide or peptidomimetic comprises about 50 or fewer amino acids and inhibits the Wnt pathway. In another aspect, the invention provides a peptide or peptidomimetic comprising at least six contiguous amino acids of the helix C domain of β-catenin (SEQ ID NO: 41), or inverse thereof, wherein the peptide or peptidomimetic comprises a total of about 50 or fewer amino acids. The invention also provides a cell comprising the peptide or peptidomimetic, a nucleic acid encoding the amino acid sequence of the peptide or peptidomimetic, and an antibody that binds to the peptide or peptidomimetic.

The invention further provides a method of inhibiting the Wnt pathway in a cell comprising introducing a peptide or peptidomimetic described herein into the cell, whereby the Wnt pathway is inhibited.

The invention also provides a method for inhibiting the growth or proliferation of a cancer cell comprising administering a peptide or peptidomimetic described herein to the cancer cell, whereupon the growth or proliferation of the cancer cell is inhibited.

In addition, the invention provides a method of treating or preventing a disease mediated by the Wnt pathway in a host comprising administering to the host a peptide or peptidomimetic described herein or nucleic acid encoding same, whereby the disease is treated or prevented.

Related compounds, compositions, and methods also are provided, as will be apparent from the detailed description of the invention.

DETAILED DESCRIPTION OF THE INVENTION

Figure 1:
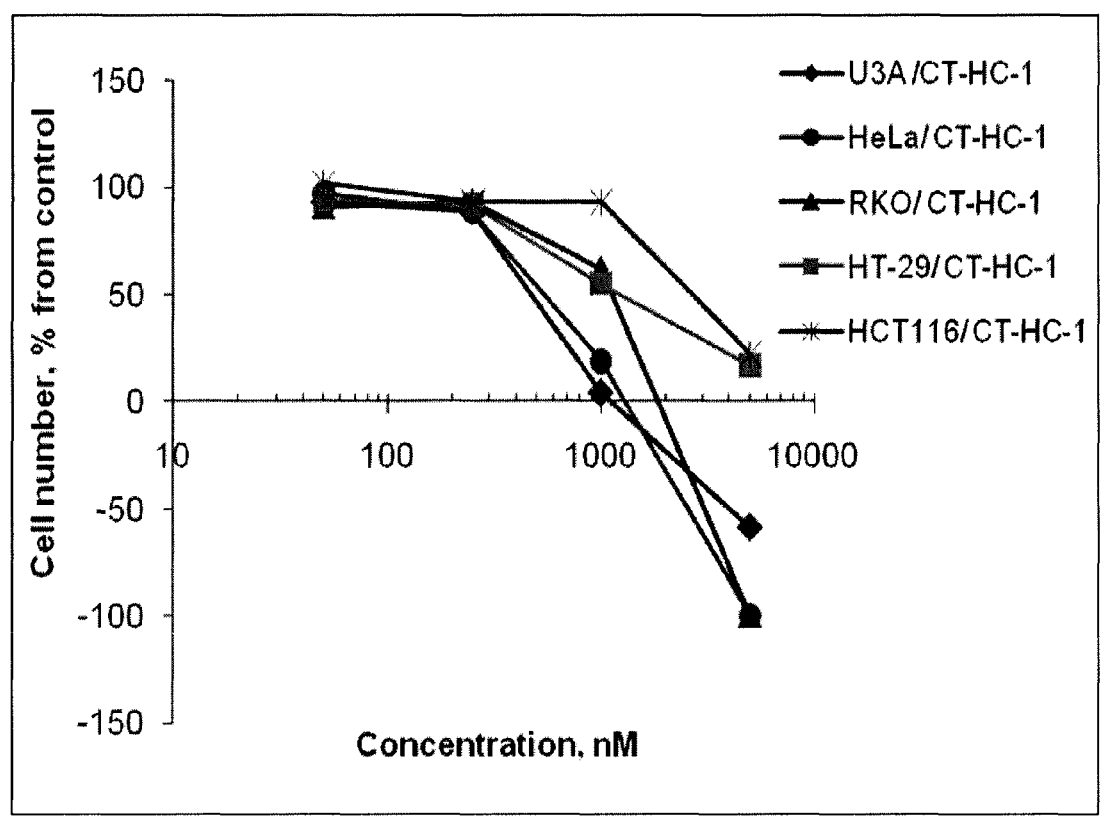
FIG. 1 is a graph depicting the growth inhibition and cancer cell death caused by the CT-HC-1 peptide inhibitor. The concentration (nM) of the CT-HC-1 peptide inhibitor is indicated on the x-axis and the cell number as a percent relative to a control is indicated on the y-axis.

The invention provides a peptide or peptidomimetic, wherein at least a portion of the amino acid sequence of the peptide or peptidomimetic is derived from or based upon the amino acid sequence of helix C of β-catenin. The following are partial sequences of the β-catenin C-terminal domain, wherein helix C of the protein is underlined.

| | | SEQ ID |
|---|---|---|
| Mouse | EAIEAEGATAPLTELLHSRNEGVATYAAAVLFRMSEDKP<u>QDYKKRLSVELTSSLFR</u>TEPM | 19 |
| Rat | EAIEAEGATAPLTELLHSRNEGVATYAAAVLFRMSEDKP<u>QDYKKRLSVELTSSLFR</u>TEPM | 20 |
| Human | EAIEAEGATAPLTELLHSRNEGVATYAAAVLFRMSEDKP<u>QDYKKRLSVELTSSLFR</u>TEPM | 21 |

|          |                                                                      | SEQ ID |
|----------|----------------------------------------------------------------------|--------|
| Bovine   | EAIEAEGATAPLTELLHSRNEGVATYAAAVLFRMSEDKP<u>QDYKKRLSVELTSSLFR</u>TEPM | 22     |
| Xenopus  | EAIEAEGATAPLTELLHSRNEGVATYAAAVLFRMSEDKP<u>QDYKKRLSVELTSSLFR</u>TEPM | 23     |
| Zebrafish | EAIEAEGATAPLTELLHSRNEGVATYAAAVLFRMSEDKP<u>QDYKKRLSVELTSSLFR</u>TEPM | 24     |
| Sea urchin | EMIEQEGATAPLTELLHSRNEGVATYAAAVLYRMSDDKP<u>QDYKKRISVELGNSLFR</u>GDSV | 25   |
| Spoonworm | EMIEQEGTTAPLTELLHSRNEGVATYAAAVLFRMSEDKP<u>QDYKKRLSVELTSSLFR</u>GEQV | 26    |
| Drosophila | EIIEQEGATGPLTDLLHSRNEGVATYAAAVLFRMSEDKP<u>QDYKKRLSIELTNSLLR</u>EDNN | 27   |
|          | *  :*.*:*************:*:*********:*: .:*    :        |        |

Positions in the partial sequence of the β-catenin C-terminal domain set forth above that are conserved are marked with an asterisk. Positions of the partial sequence showing variation are marked with dots indicating the relative similarity between the residues that occupy a given position in the sequence. Two dots below a given position in the sequence indicate substitution by more closely related residues and one dot or no dots indicates substitution by less similar residues. The above alignment of a partial sequence of the β-catenin C-terminal domain shows that most of β-catenin helix C is conserved between species.

According to one aspect of the invention, the peptide or peptidomimetic comprises the amino acid sequence KKRLSVXLTSSLFR (SEQ ID NO: 1). "X" in the sequence preferably is an acidic or uncharged polar amino acid, such as Glu or Gln.

A peptide or peptidomimetic comprising the amino acid sequence KKRLSVXLTSSLFR (SEQ ID NO: 1) can further comprise one or more flanking residues. By way of illustration, SEQ ID NOs: 2-6, 8-12, 14-18, and 40 comprise the amino acid sequence KKRLSVXLTSSLFR (SEQ ID NO: 1) and one or more flanking residues (Table 1). The flanking residues should be chosen so as not to interfere with the ability of the peptide to inhibit the Wnt pathway. Guidance for the selection of such residues is provided by the relevant sequence of the helix C region of β-catenin itself. For instance, one can choose residues for use in the peptide that are identical to, or have properties similar to, the residues at the corresponding positions of the helix C region of a given β-catenin (preferably human β-catenin). In particular, one or more flanking residues can be selected from the catenin primary sequence as set forth above or as set forth in SEQ ID NO: 42, wherein X is any amino acid, preferably an acidic or uncharged polar amino acid, such as Glu or Gln. By way of further illustration, the peptide or peptidomimetic can comprise, consist essentially of, or consist of a fragment of SEQ ID NO: 42.

Preferably, the amino acid used at the "$X_1$," "$X_2$," "$X_3$," "$X_4$," or "$X_5$" residues of SEQ ID NOs: 2-6, 8-12, 14-18, and 40 has one or more of the properties of columns (A)-(E) of Table 2 for that residue. More preferably, the selected amino acid residue has more than one of such indicated properties or even all such indicated properties. By way of further illustration, Table 2 provides exemplary amino acid residues to be used at each position "$X_1$," "$X_2$," "$X_3$," "$X_4$," or "$X_5$" of SEQ ID NOs: 2-6, 8-12, 14-18, and 40, wherein the most preferred residues are underlined. Of course, other amino acid residues, including synthetic amino acid residues, can be used instead of the exemplary residues, which are provided only for illustration. Specific examples of amino acid sequences comprising the amino acid sequence KKRLSVXLTSSLFR (SEQ ID NO: 1) include SEQ ID NOs: 28-33, 35-39, and 43-49.

TABLE 1

| SEQ ID NO: | Peptide Sequence |
|---|---|
| 1 | KKRLSVXLTSSLFR |
| 2 | $X_3$KKRLSVXLTSSLFR |
| 3 | $X_3$KKRLSVXLTSSLFR$X_4$ |
| 4 | KKRLSVXLTSSLFR$X_4$ |
| 5 | KKRLSVXLTSSLFR$X_4X_5$ |
| 6 | $X_3$KKRLSVXLTSSLFR$X_4X_5$ |
| 7 | KKRLSVELTSSLFR |
| 8 | $X_3$KKRLSVELTSSLFR |
| 9 | $X_3$KKRLSVELTSSLFR$X_4$ |
| 10 | KKRLSVELTSSLFR$X_4$ |
| 11 | KKRLSVELTSSLFR$X_4X_5$ |
| 12 | $X_3$KKRLSVELTSSLFR$X_4X_5$ |
| 13 | KKRLSVQLTSSLFR |
| 14 | $X_3$KKRLSVQLTSSLFR |
| 15 | $X_3$KKRLSVQLTSSLFR$X_4$ |
| 16 | KKRLSVQLTSSLFR$X_4$ |
| 17 | KKRLSVQLTSSLFR$X_4X_5$ |
| 18 | $X_3$KKRLSVQLTSSLFR$X_4X_5$ |
| 40 | $X_1X_2X_3$YKKRLSVELTSSLFR |

Most preferably, $X_1$, $X_2$, $X_3$, $X_4$, and $X_5$, to the extent the residues are present in the sequence, are selected to be Lys (or Pro), Gln, Tyr (or Asn or Asp), Thr, and Glu (or Asp), respectively.

TABLE 2

| | Preferred Amino Acid | | |
|---|---|---|---|
| | (A) Polarity | (B) Charge | (C) Exemplary[†] |
| $X_1$ | Nonpolar or Polar | Uncharged or negative | <u>K</u>, R, H, <u>P</u>, A, G, V, L, I, F, M, W |
| $X_2$ | Polar | Uncharged | <u>Q</u>, N, S, T, Y |

TABLE 2-continued

| | Preferred Amino Acid | | |
|---|---|---|---|
| | (A) Polarity | (B) Charge | (C) Exemplary† |
| $X_3$ | Polar | Neutral | Y, T, S, N, Q, D |
| $X_4$ | Polar | Uncharged | T, Y, S, N, Q, G |
| $X_5$ | Polar | Negative or uncharged | E, Q, D, N |

†Underlining indicates preferred residues.

According to another aspect of the invention, the peptide or peptidomimetic comprises the helix C region of β-catenin or a fragment thereof comprising about eight or more contiguous amino acids (e.g., 9 or more, 10 or more, 11 or more, 12 or more, 13 or more, 14 or more, 15 or more, or 16 or more) contiguous amino acids.

Variant sequences other than those specifically mentioned herein are contemplated, which comprise significant sequence identity (e.g., 80%, 85%, 90%, 95%, 98%, or 99% sequence identity) to the amino acid sequence of the helix C region of β-catenin (e.g., SEQ ID NO: 19) or fragment thereof comprising at least eight contiguous amino acids, provided that such variants retain the ability to inhibit the Wnt pathway. Such variants can comprise one or more (e.g., two or more, three or more, four or more, or five or more) amino acid substitutions, deletions, or insertions as compared to the parent amino acid sequence. Conservative amino acid substitutions are known in the art, and include amino acid substitutions in which one amino acid having certain physical and/or chemical properties is exchanged for another amino acid that has the same or similar chemical or physical properties. For instance, the conservative amino acid substitution can be an acidic amino acid substituted for another acidic amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Val, etc.), a basic amino acid substituted for another basic amino acid (Lys, Arg, etc.), an amino acid with a polar side chain substituted for another amino acid with a polar side chain (Asn, Cys, Gln, Ser, Thr, Tyr, etc.), etc. Desirably, the peptide or peptidomimetic comprises one or more of SEQ ID NOs: 28-33, 35-39, and 43-49 or a variant thereof comprising up to five substitutions or deletions (e.g., one, two, three, or four substitutions or deletions), such as SEQ ID NO: 34.

The peptide or peptidomimetic also can comprise synthetic, non-naturally occurring amino acids. Such synthetic amino acids include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, α-tert-butylglycine, and 2-(4-pentenyl)-alanine. The properties of such synthetic amino acids are well-documented. Any natural amino acid of one or more of the sequences discussed herein can be substituted with a synthetic amino acid having similar properties.

The term "peptidomimetic" as used herein refers to a compound that comprises the same general structure of a corresponding polypeptide, but which includes modifications that increase its stability or biological function. For instance, the peptidomimetic can be a "reverso" analogue of a given peptide, which means that the peptidomimetic comprises the reverse sequence of the peptide. In addition, or instead, the peptidomimetic can comprise one or more amino acids in a "D" configuration (e.g., D-amino acids), providing an "inverso" analogue. Peptidomimetics also include peptoids, wherein the side chain of each amino acid is appended to the nitrogen atom of the amino acid as opposed to the alpha carbon. Peptoids can, thus, be considered as N-substituted glycines which have repeating units of the general structure of $NRCH_2CO$ and which have the same or substantially the same amino acid sequence as the corresponding polypeptide. In this respect, the peptide or peptidomimetic can comprise any of the sequences described herein in reverse order.

Smaller peptides and peptidomimetics are believed to be advantageous for inhibiting the Wnt pathway and to facilitate entry into a cell. Thus, the peptide or peptidomimetic preferably comprises about 50 or fewer amino acids, such as about 40 or fewer amino acids, about 35 or fewer amino acids, about 25 or fewer amino acids, or even about 20 or fewer amino acids. Generally, however, the peptide or peptidomimetic will comprise at least about 8 amino acids, such as at least about 10 amino acids, at least 12 amino acids, or at least about 14 amino acids.

The peptide or peptidomimetic can comprise, consist essentially of, or consist of, any of foregoing sequences or variants thereof. The peptide or peptidomimetic consists essentially of the foregoing sequences if it does not comprise other elements, such as other amino acid sequences, that prevent the peptide from inhibiting the Wnt pathway.

The peptide or peptidomimetic coupled to a cell penetrating motif or other moiety so as to more efficiently facilitate the delivery of the peptide to the interior of a cell, anchor the peptide to the cell membrane of a cell, and/or promote folding of the peptide. Thus, the peptide or peptidomimetic can be provided as part of a composition comprising the peptide and cell penetrating motif or other moiety. Any of various cell penetrating motifs and or other moieties useful for these purposes can be used. By way of illustration, suitable cell penetrating motifs and other relevant moieties (e.g., cell-membrane anchoring moieties) include lipids and fatty acids, peptide transduction domains (e.g., HIV-TAT, HSV Transcription Factor (VP22), and penetratin), and other types of carrier molecules (e.g., Pep-1).

According to one aspect of the invention, the cell penetrating motif or other moiety comprises a fatty acid or lipid molecule. The fatty acid or lipid molecule can be, for example, a palmitoyl group, farnesyl group (e.g., farnesyl diphosphate), a geranylgeranyl group (e.g., geranylgeranyl diphosphate), a phospholipid group, glycophosphatidylinositol, phosphatidylserine, phosphatidylethanolamine, sphingomyelin, phosphatidylcholine, cardiolipin, phosphatidylinositol, phosphatidic acid, lysophosphoglyceride, a cholesterol group, and the like. Preferably, the fatty acid molecule is a $C_1$ to $C_{24}$ fatty acid or $C_8$ to $C_{16}$ fatty acid. Desirably, the fatty acid comprises 3 or more, 4 or more, 5 or more, 6 or more, 7 or more, 8 or more, 9 or more, or 10 or more carbon atoms. Typically, the fatty acid will comprise 22 or fewer, 20 or fewer, 18 or fewer, or 16 or fewer carbon atoms. Specific examples of fatty acids include, without limitation, lauric acid, palmitic acid, myristic acid, lauric acid, capric acid, stearic acid, oleic acid, linoleic acid, α-linoleic acid, linolenic acid, arachidonic acid, timnodonic acid, docosohexenoic acid, erucic acid, arachidic acid, behenic acid.

The fatty acid or lipid molecule can be attached to any suitable part of the peptide or peptidomimetic. In a preferred embodiment of the invention, the fatty acid or lipid molecule is attached at the amino (N-) terminus, the carboxyl (C-) terminus, both the N- and C-termini, or the ε-amino group of a terminal Lys residue of the peptide or peptidomimetic. Typically, the fatty acid or lipid molecule is attached via an amide or ester linkage. When the fatty acid or lipid molecule is attached at the C-terminus of the polypeptide or peptidomimetic, the fatty acid or lipid molecule preferably is modified, e.g., to include an amino group such as $NH_2(CH_2)_n$ COOH or $CH_3(CH_2)_m CH(NH_2)COOH$, wherein each of n and m is, independently, 1 to 24, preferably 8 to 16. The fatty acid or lipid residue can advantageously be attached to a terminal lysine in the epsilon (ε) position.

According to another aspect of the invention, the cell penetrating motif is a peptide transduction domain (also known as protein transduction domains or PTDs). PTDs typically are fused to the inhibitory peptide or peptidomimetic. Thus, the peptide or peptidomimetic can be a fusion protein comprising the peptide or peptidomimetic and a PTD. Often, the fusion protein is cleaved inside of a cell to remove the cell penetrating motif.

The peptide or peptidomimetic can further comprise linking residues disposed between the amino acid sequence derived from or based upon the helix C region of β-catenin and the cell penetrating motif or other moiety. Illustrative examples of such linking residues include K, KK, RK, RQ, KQ, RQI, KQI, RQIK, and KQIK.

The peptide or peptidomimetic can be prepared by any method, such as by synthesizing the peptide or peptidomimetic, or by expressing a nucleic acid encoding an appropriate amino acid sequence in a cell and harvesting the peptide from the cell. Of course, a combination of such methods also can be used. Methods of de novo synthesizing peptides and peptidomimetics, and methods of recombinantly producing peptides and peptidomimetics are known in the art (see, e.g., Chan et al., *Fmoc Solid Phase Peptide Synthesis*, Oxford University Press, Oxford, United Kingdom, 2005; *Peptide and Protein Drug Analysis*, ed. Reid, R., Marcel Dekker, Inc., 2000; *Epitope Mapping*, ed. Westwood et al., Oxford University Press, Oxford, United Kingdom, 2000; Sambrook et al., *Molecular Cloning: A Laboratory Manual*, 3rd ed., Cold Spring Harbor Press, Cold Spring Harbor, N.Y. 2001; and Ausubel et al., *Current Protocols in Molecular Biology*, Greene Publishing Associates and John Wiley & Sons, NY, 1994).

The invention also provides a nucleic acid encoding the amino acid sequence of the peptide or peptidomimetic. The nucleic acid can comprise DNA or RNA, and can be single or double stranded. Furthermore, the nucleic acid can comprise nucleotide analogues or derivatives (e.g., inosine or phophorothioate nucleotides and the like). The nucleic acid can encode the amino acid sequence of the peptide or peptidomimetic alone, or as part of a fusion protein comprising such sequence and a cell penetrating motif, as described herein. The nucleic acid encoding the amino acid sequence of the peptide or peptidomimetic can be provided as part of a construct comprising the nucleic acid and elements that enable delivery of the nucleic acid to a cell, and/or expression of the nucleic acid in a cell. Such elements include, for example, expression vectors and transcription and/or translation sequences. Suitable vectors, transcription/translation sequences, and other elements, as well as methods of preparing such nucleic acids and constructs, are known in the art (e.g., Sambrook et al., supra; and Ausubel et al., supra).

The present invention further provides an antibody to the peptide or peptidomimetic, or an antigen binding fragment or portion thereof (e.g., Fab, F(ab')$_2$, dsFv, sFv, diabodies, and triabodies). The antibody can be monoclonal or polyclonal, and of any isotype, e.g., IgA, IgD, IgE, IgG, IgM, etc. The antibody can be a naturally-occurring antibody, e.g., an antibody isolated and/or purified from a mammal, e.g., mouse, rabbit, goat, horse, chicken, hamster, human, etc. Alternatively, the antibody can be a synthetic or genetically-engineered antibody, e.g., a humanized antibody or a chimeric antibody. The antibody can be in monomeric or polymeric form. The antibody, or antigen binding portion thereof, can be modified to comprise a detectable label, such as, for instance, a radioisotope, a fluorophore (e.g., fluorescein isothiocyanate (FITC), phycoerythrin (PE)), an enzyme (e.g., alkaline phosphatase, horseradish peroxidase), or element particles (e.g., gold particles). Such antibodies can be used for any purpose, such as to facilitate the detection or purification of a peptide or peptidomimetic described herein. Suitable methods of making antibodies are known in the art, including standard hybridoma methods, EBV-hybridoma methods, bacteriophage vector expression systems, and phage-display systems (see, e.g., Köhler and Milstein, *Eur. J. Immunol.*, 5, 511-519 (1976); Harlow and Lane (eds.), *Antibodies: A Laboratory Manual*, CSH Press (1988); C. A. Janeway et al. (eds.), *Immunobiology*, 5th Ed., Garland Publishing, New York, N.Y. (2001); Haskard and Archer, *J. Immunol. Methods*, 74(2), 361-67 (1984); Roder et al., *Methods Enzymol.*, 121, 140-67 (1986); Huse et al., *Science*, 246, 1275-81 (1989); Sambrook et al., supra; Ausubel et al., supra; Knappik et al., *J. Mol. Biol.* 296: 57-86 (2000)).

The peptide or peptidomimetic, nucleic acid, or antibody can be isolated. The term "isolated" as used herein encompasses compounds or compositions that have been removed from a biological environment (e.g., a cell, tissue, culture medium, body fluid, etc.), or otherwise increased in purity to any degree (e.g., isolated from a synthesis medium). Isolated compounds and compositions, thus, can be synthetic or naturally produced.

A cell comprising the peptide or peptidomimetic, or nucleic acid encoding the amino acid sequence of the peptide or peptidomimetic, also is provided herein. Such a cell includes, for example, a cell engineered to express a nucleic acid encoding the amino acid sequence of the peptide or peptidomimetic. Suitable cells include prokaryotic and eukaryotic cells, e.g., mammalian cells, yeast, fungi, and bacteria (such as *E. coli*). The cell can be in vitro, as is useful for research or for production of the peptide or peptidomimetic, or the cell can be in vivo, for example, in a transgenic mammal that expresses the peptide.

Desirably, the peptide or peptidomimetic inhibits the Wnt pathway or otherwise inhibits cell growth or proliferation, especially that of a cancer cell. For the purposes of this invention, a compound inhibits cell growth if it reduces cell proliferation or growth to any degree as compared to the cell proliferation or growth of the same cell (or cell of the same type) in the absence of the inhibitor. Similarly, a compound inhibits Wnt signaling if it reduces the level Wnt signaling to any degree as compared to the level of Wnt signaling in the absence of the compound. The level of Wnt signaling can be measured by any appropriate metric, such as by the level of β-catenin activity and/or amount of β-catenin protein. In a preferred embodiment, the peptide or peptidomimetic inhibits the Wnt pathway to a degree sufficient to reduce the rate of cell growth of a cancer cell, and/or induce cell death of a cancer cell. Suitable assays to test for such an inhibition of the Wnt pathway (and, in particular, β-catenin) are known in the art, including binding affinity assays, cell growth and cytotoxicity assays, and gene regulation assays (e.g., luciferase reporter assay).

The peptide or peptidomimetic can be used for any purpose, but is especially useful for inhibiting the Wnt pathway in a cell. Thus, provided herein is a method of inhibiting the Wnt pathway in a cell, which method comprises administering a peptide or peptidomimetic described herein to a cell in an amount sufficient to inhibit the Wnt pathway.

The peptide or peptidomimetic can be administered to the cell by any method. For example, the peptide or peptidomimetic can be administered to a cell by contacting the cell with the peptide or peptidomimetic, typically in conjunction with a regent or other technique (e.g., microinjection or electroporation) that facilitates cellular uptake. Alternatively, and preferably, the peptide or peptidomimetic is administered by contacting the cell with a composition comprising the peptide or peptidomimetic and a cell penetrating motif, as discussed herein.

The peptide or peptidomimetic also can be administered by introducing a nucleic acid encoding the amino acid sequence of the peptide into the cell such that the cell expresses a peptide comprising the amino acid sequence. The nucleic acid encoding the peptide can be introduced into the cell by any of various techniques, such as by contacting the cell with the nucleic acid or a composition comprising the nucleic acid as part of a construct, as described herein, that enables the delivery and expression of the nucleic acid. Specific protocols for introducing and expressing nucleic acids in cells are known in the art (see, e.g., Sambrook et al. (eds.), supra; and Ausubel et al., supra).

The peptide, peptidomimetic, or nucleic acid can be administered to a cell in vivo by administering the peptide, peptidomimetic, or nucleic acid comprising the cell. The host can be any host, such as a mammal, preferably a human. Suitable methods of administering peptides, peptidomimetics, and nucleic acids to hosts are known in the art, and discussed in greater detail in connection with the pharmaceutical composition comprising such compounds, below.

The cell can be any type of cell that comprises β-catenin. Preferably, the cell is of a type that is related to a disease or condition mediated by the Wnt pathway. For example, the cell can be an engineered cell that is designed to mimic a condition or disease associated with an aberrant Wnt pathway, or the cell can be a cell of a patient afflicted with a disease or condition associated with an aberrant Wnt pathway. Diseases associated with an aberrant Wnt pathway include diseases characterized by activation of the Wnt signaling pathway leading to β-catenin overexpression, up-regulation, and/or overabundance. Cancer cells are one example of a cell type that can be used. The cell can be in vitro or in vivo in any type of animal, such as a mammal, preferably a human.

The method of inhibiting the Wnt pathway in a cell can be used for any purpose, such as for the research, treatment, or prevention of diseases or conditions mediated by aberrant Wnt signaling. Aberrant Wnt signaling has been linked to a variety of cancers. Thus, according to one aspect of the method of the invention, the peptide or peptidomimetic is administered to a cancer cell, in vitro or in vivo, and administration of the peptide or peptidomimetic to the cancer cell inhibits the growth or survival of the cancer cell.

The cancer cell can be a cell of any type of cancer, in vitro or in vivo, particularly those associated with aberrant Wnt signaling, such as those associated with β-catenin overexpression, up-regulation, and/or overabundance. Non-limiting examples of specific types of cancers include cancer of the head and neck, eye, skin, mouth, throat, esophagus, chest, bone, lung, colon, sigmoid, rectum, stomach, prostate, breast, ovaries, kidney, liver, pancreas, brain, intestine, heart or adrenals. The cancers can include solid tumor, sarcoma, carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendothelio sarcoma, synovioma, mesothelioma, Ewing's tumor, leiomyosarcoma, rhabdomyosarcoma, colon carcinoma, pancreatic cancer, breast cancer, ovarian cancer, prostate cancer, hepatocellular cancer, gastric cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, Kaposi's sarcoma, pinealoma, hemangioblastoma, acoustic neuroma, oligodendroglioma, menangioma, melanoma, neuroblastoma, retinoblastoma, a blood-born tumor, acute lymphoblastic leukemia, acute lymphoblastic B-cell leukemia, acute lymphoblastic T-cell leukemia, acute myeloblastic leukemia, acute promyelocytic leukemia, acute monoblastic leukemia, acute erythroleukemic leukemia, acute megakaryoblastic leukemia, acute myelomonocytic leukemia, acutenonlymphocytic leukemia, acute undifferentiated leukemia, chronic myelocytic leukemia, chronic lymphocytic leukemia, hairy cell leukemia, or multiple myeloma. See, e.g., Harrison's Principles of Internal Medicine, Eugene Braunwald et al., eds., pp. 491-762 (15th ed. 2001). The methods of the invention are believed to be especially useful for the treatment of pancreatic cancer, lung cancer, prostate cancer, gastrointestinal tumors, leukemia, head and neck squamous cell carcinoma, desmoid tumors, endometrial tumors, hepatocellular tumors, ovarian tumors, thyroid tumors, uterine tumors, breast tumors, Barret's esophagus, Burkitt's lymphoma, medulloblastoma, Wilms' tumor, neuroblastoma, hepatoblastoma, as well as any other cancer known to be responsive to Wnt pathway inhibitors.

The inventive peptides or peptidomimetics also can be used to treat diabetes, hair loss, bone fracture, bone disease, bone injury, loss of bone mass, diseases of the sweat glands, and disease of the mammary glands.

Peptides and peptidomimetics, as described herein, include salts, esters, alkylated (e.g., methylated), and acetylated peptides. Any one or more of the compounds or compositions of the invention described herein (e.g., peptide or peptidomimetic, nucleic acid, antibody, or cell) can be formulated as a pharmaceutical composition, comprising a compound of the invention and a pharmaceutically acceptable carrier. Furthermore, the compounds or compositions of the invention can be used in the methods described herein alone or as part of a pharmaceutical formulation.

The pharmaceutical composition can comprise more than one compound or composition of the invention. Alternatively, or in addition, the pharmaceutical composition can comprise one or more other pharmaceutically active agents or drugs. Examples of such other pharmaceutically active agents or drugs that may be suitable for use in the pharmaceutical composition include anticancer agents. Suitable anticancer agents include, without limitation, alkylating agents; nitrogen mustards; folate antagonists; purine antagonists; pyrimidine antagoinists; spindle poisons; topoisomerase inhibitors; apoptosis inducing agents; angiogenesis inhibitors; podophyllotoxins; nitrosoureas; cisplatin; carboplatin; interferon; asparginase; tamoxifen; leuprolide; flutamide; megestrol; mitomycin; bleomycin; doxorubicin; irinotecan; and taxol, geldanamycin (e.g., 17-AAG), and various anti-cancer peptides and antibodies.

The carrier can be any of those conventionally used and is limited only by physio-chemical considerations, such as solubility and lack of reactivity with the active compound(s), and by the route of administration. The pharmaceutically acceptable carriers described herein, for example, vehicles, adjuvants, excipients, and diluents, are well-known to those skilled in the art and are readily available to the public. It is preferred that the pharmaceutically acceptable carrier be one which is chemically inert to the active agent(s) and one which has no detrimental side effects or toxicity under the conditions of use.

The choice of carrier will be determined in part by the particular compound or composition of the invention and other active agents or drugs used, as well as by the particular method used to administer the compound and/or inhibitor. Accordingly, there are a variety of suitable formulations of the pharmaceutical composition of the present inventive methods. The following formulations for oral, aerosol, parenteral, subcutaneous, intravenous, intramuscular, interperitoneal, rectal, and vaginal administration are exemplary and are in no way limiting. One skilled in the art will appreciate that these routes of administering the compound of the invention are known, and, although more than one route can be used to administer a particular compound, a particular route can provide a more immediate and more effective response than another route.

Injectable formulations are among those formulations that are preferred in accordance with the present invention. The requirements for effective pharmaceutical carriers for injectable compositions are well-known to those of ordinary skill in the art (See, e.g., Pharmaceutics and Pharmacy Practice, J.B. Lippincott Company, Philadelphia, Pa., Banker and Chalmers, eds., pages 238-250 (1982), and ASHP Handbook on Injectable Drugs, Toissel, 4th ed., pages 622-630 (1986)).

Topical formulations are well-known to those of skill in the art. Such formulations are particularly suitable in the context of the present invention for application to the skin.

Formulations suitable for oral administration can consist of (a) liquid solutions, such as an effective amount of the inhibitor dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

The compounds and compositions of the invention, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer. Such spray formulations also may be used to spray mucosa.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compounds and compositions of the invention can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, dimethylsulfoxide, glycerol ketals, such as 2,2-dimethyl-1,3-dioxolane-4-methanol, ethers, such as poly (ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-b-aminopropionates, and 2-alkyl-imidazoline quaternary ammonium salts, and (e) mixtures thereof.

Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Additionally, the compounds of the invention, or compositions comprising such compounds, can be made into suppositories by mixing with a variety of bases, such as emulsifying bases or water-soluble bases. Formulations suitable for vaginal administration can be presented as pessaries, tampons, creams, gels, pastes, foams, or spray formulas containing, in addition to the active ingredient, such carriers as are known in the art to be appropriate.

The following examples further illustrate the invention but, of course, should not be construed as in any way limiting its scope.

EXAMPLE 1

This example demonstrates the synthesis of the inventive peptides and peptidomimetics.

Several peptides were synthesized with sequences based on helix C of β-catenin. Without wishing to be bound by any particular theory, it is believed that β-catenin helix C and the synthetic peptides based on helix C as disclosed herein interact with the last armadillo repeat of β-catenin. More specifically, it is believed that the amino acid residues corresponding to Leu674, Leu678, and Leu682 of native, human β-catenin helix C fit into a hydrophobic groove formed by the second and third helices of armadillo repeat 12. Also, it is thought that Lys681 may form an ion pair with Glu664, while Arg684 may form a hydrogen bond with Ser646. The sequence of the synthetic peptides is set forth in Table 3:

TABLE 3

| Inhibitor | Sequence | SEQ ID NO: |
|---|---|---|
| CT-HC-1 | Pal-ε-KYKKRLSVELTSSLFR | 28 |
| CT-HC-14 | Pal-PQNYKKRLSVELTSSLFR | 29 |
| CT-HC-12 | Pal-YKKRLSVELTSSLFR | 30 |
| CT-HC-2 | Pal-ε-KQDYKKRLSVELTSSLFR | 31 |
| CT-HC-3 | Pal-ε-KYKKRLSVQLTSSLFR | 32 |
| CT-HC-8 | Doa-YKKRLSVELTSSLFR | 33 |
| CT-HC-9 | Ac-YKKRLS+ELT+SLFR (Stapled) | 34 |
| CT-HC-4 | Ac-RFLSSTLEVSLRKKYK-ε-Pal (All-D) | 35 |
| CT-HC-5 | Pal-TRFLSSTLEVSLRKK-NH$_2$ (All-D) | 36 |
| CT-HC-10 | Pal-TRFLSSTLEVSLRKKY-NH$_2$ (All-D) | 37 |
| CT-HC-11 | Pal-Aib-RFLSSTLEVSLRKKY-NH$_2$ (All-D) | 38 |
| CT-HC-6 | Pal-ε-KTRFLSSTLEVSLRKK-NH$_2$ (All-D) | 39 |

Doa = 2-dodecyl-alanine
Aib = amino-isobutyric acid
+ = 2-(4'-pentenyl)alanine (which is involved in hydrocarbon stapling of the peptide)
Ac = acetyl Since negative charges of peptides impede cell membrane penetration, the residue corresponding to Glu677 of the native helix C sequence was replaced with Gln in CT-HC-3. According to structural data, this residue is not believed to be involved in intra-molecular interactions. CT-HC-5, CT-HC-6, CT-HC-10, and CT-HC-11 are retro-inverso derivatives constructed from all-D amino acids, which were designed to improve metabolic stability. CT-HC-11 has amino-isobutyric acid on the N-terminus, which is believed to stabilize the helical conformation of peptides. CT-HC-8 has the same amino acid sequence as CT-HC-1 except CT-HC-8 lacks the N-terminal palmitoyl-ε-lysine residue and has a novel amino acid, 2-dodecyl-alanine, that is believed to provide both membrane anchoring and stabilization of the helical fold.

The peptides were synthesized on a 433A Peptide Synthesizer (Applied Biosystems) or Liberty Microwave Synthesizer (CEM Corporation) using Fmoc chemistry. The peptides were cleaved from the resin and deprotected with a mixture of 90.0% (v/v) trifluoroacetic acid (TFA) with 2.5% water, 2.5% triisopropyl-silane, and 5% thioanisol. The resin and deprotection mixture were pre-chilled to −5° C. and reacted for 15 minutes at −5° C. with stirring. The reaction was allowed to continue at room temperature for 1.75 hours. The resin was filtered off and the product was precipitated with cold diethyl ether. The resin was washed with neat TFA. Peptide suspended in diethyl ether was centrifuged at −20° C. and the precipitate was washed with diethyl ether four more times and left to dry in a vacuum overnight. The dried crude peptide was dissolved in DMSO and purified on a preparative (25 mm×250 mm) Atlantis C18 reverse phase column (Agilent Technologies) in a 90 minute gradient of 0.1% (v/v) trifluoroacetic acid in water and 0.1% trifluoroacetic acid in acetonitrile, with a 10 mL/min flow rate. The fractions containing peptides were analyzed on Agilent 1100 LC/MS spectrometer with the use of a Zorbax 300SB-C3 Poroshell column and a gradient of 5% acetic acid in water and acetonitrile. Fractions that were more than 95% pure were combined and freeze dried. Retro-inverso peptide made of all-D amino acids was synthesized using essentially the same protocol, except that palmitic acid had to be introduced in the side chain. Resin preloaded with α-Fmoc-ε-palmytoil-D-Lys was prepared as described (Remsberg et al., *J. Med. Chem.*, 50: 4534-4538 (2007)). Purity (>95%) and structure of all peptides were confirmed by mass spectrometry using Agilent C18 reversed-phase columns (4.6×150 mm) and an Agilent 1100 LC/MS system.

EXAMPLE 2

This example demonstrates the use of the peptides and peptidomimetics of the invention to inhibit cell growth in various cell lines.

HeLa, U3A, RKO, HCT-116, and HT-29 cells were exposed to the CT-HC-1, CT-HC-3, CT-HC-5, and CT-HC-8 inhibitors of Example 1 for 48 hours in medium containing 1% bovine fetal serum, and the resulting cell number was evaluated using a MTT assay. Each of these cell lines is relevant to the evaluation of Wnt signaling. Cervical carcinoma HeLa cells overexpress β-catenin (see, e.g., Lee et al., *Int. J. Cancer*, 124(2): 287-297 (2009); and Lee et al., *Gynecol. Oncol.*, 109(2): 270-274 (2008)). β-catenin is activated in colon carcinoma RKO due to mutation in CDX2 (see, e.g., Dang et al., *Oncogene*, 20(35): 4884-4890 (2001)). Colon adenocarcinoma HCT116 has elevated mutated β-catenin; however, it was found in the past to be resistant to down regulation of β-catenin (see, e.g., Chan et al., *Proc. Natl. Acad. Sci. USA*, 99(12): 8265-8270 (2002); and Handeli et al., *Mol. Cancer Ther.*, 7(3): 521-529 (2008)). Colon carcinoma HT-29 has truncated adenomatous polyposis coli (APC) protein, which is a common cause of canonical Wnt pathway activation in colon malignancies. Fibrosarcoma U3A cells are STAT1-negative and have uncharacterized status of Wnt pathway.

As demonstrated by the data set forth in Table 4, all tested cancer cell lines were sensitive to the inventive peptide inhibitors. CT-HC-8, which lacks a palmitoyl residue, required much higher concentrations to inhibit the cell lines. Lipidation of the peptide inhibitors is believed to enhance cell penetration and structure stabilization of the peptide inhibitors, leading to improved biological activity of the peptide inhibitors.

TABLE 4

| Inhibitor | $GI_{50}$ nM | | | | |
|---|---|---|---|---|---|
| | HeLa | U3A | RKO | HCT-116 | HT-29 |
| CT-HC-1 | 630 ± 25 | 600 ± 40 | 1300 ± 50 | 3400 ± 250 | 1400 ± 50 |
| CT-HC-3 | 800 ± 80 | 650 ± 45 | 1800 ± 150 | 4000 ± 300 | 2800 ± 100 |
| CT-HC-5 | 1200 ± 90 | 1500 ± 100 | 1150 ± 50 | 2400 ± 400 | 2000 ± 100 |
| CT-HC-8 | 3200 ± 400 | >5000 | >5000 | >5000 | >5000 |

The ability of CT-HC-1 to inhibit growth and to kill cancer cells at different concentrations was further investigated in HeLa, U3A, RKO, HCT-116, and HT-29 cells. The cells were stained with Promega Non-Radioactive Cell Proliferation Assay Kit (MTT) according to the manufacture's protocol. The absorbance of the wells was determined at 544 nm by a FLUOstar/POLARstar Galaxy (BMG Lab Technologies GmbH) Microplate Reader. The assays were performed on control (C) and test (T) cells. Untreated cells were used as a control. Cellular responses were calculated from the data using the following formula: $100 \times [(T-T_0)/(C-T_0)]$ for $T > T_0$ and $100 \times [(T-T_0)/T_0]$ for $T < T_0$. $T_0$ corresponds to cell density at the time of drug addition. As demonstrated by FIG. 1, administration of CT-HC-1 decreased cell numbers in a concentration dependent manner as compared to untreated cells.

HCT-116 cells showed somewhat lower sensitivity towards the peptide inhibitors (see Table 4 and FIG. 1). This result correlates well with the data for other Wnt inhibitors (see, e.g., Handeli et al., supra) and CTNNB1 gene disruption in HCT-116 cell line (see, e.g., Chan et al., supra). It is believed that helix C based inhibitors may cause destabilization of β-catenin structure and degradation, most likely through ubiquitination pathway. The mutated version of β-catenin present in HCT-116 cells is known to be resistant to ubiquitination, which may explain the difference in sensitivity to the inhibitors.

Figure 2A:
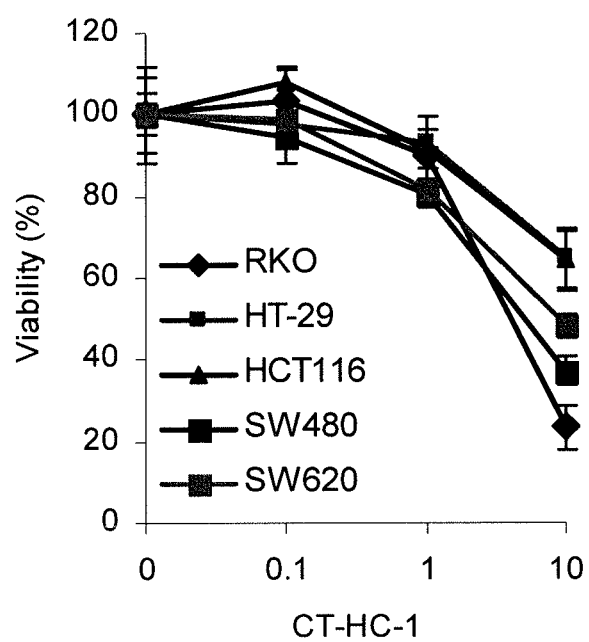
FIGS. 2A-C are graphs depicting the suppression of cell viability of colon cancer cells (RKO, HT-29, HCT116, SW480, and SW620) by the CT-HC-1 (A), CT-HC-3 (B), and CT-HC-5 (C) peptide inhibitors. The concentration (μM) of the peptide inhibitor is indicated on the x-axis and the percent viability is indicated on the y-axis.
Figure 2B:
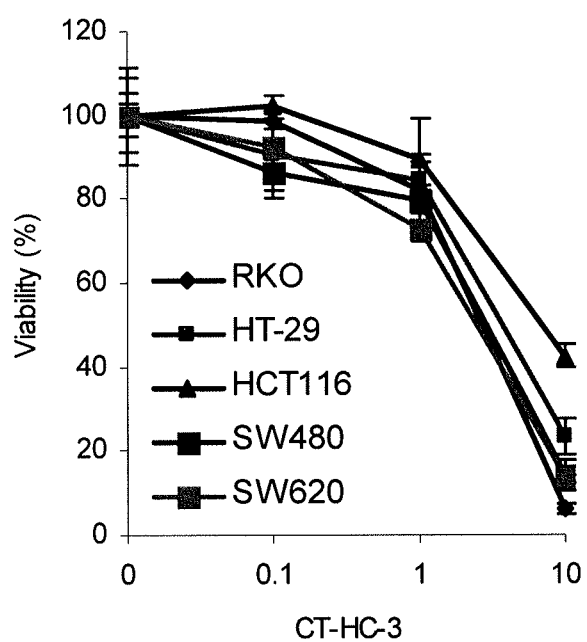
Figure 2C:
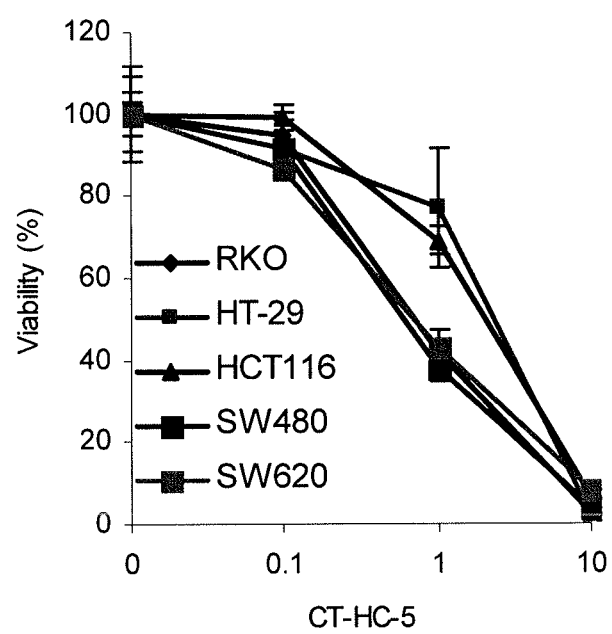

A similar experiment was performed using RKO, HT-29, HCT-116, SW-480, and SW-620 cells. Colorectal adenocarcinoma SW-480 and SW-620 cells have truncated APC protein, which—as discussed above—is a common cause of canonical Wnt pathway activation in colon malignancies. As demonstrated by FIGS. 2A-C, increasing concentrations of the CT-HC-1, CT-HC-3, and CT-HC-8 inhibitors resulted in decreased viability of the RKO, HT-29, HCT-116, SW-480, and SW-620 cells.

EXAMPLE 3

This example further illustrates the use of the inventive peptides and peptidomimetics to inhibit cell growth via Wnt signaling.

Primary metanephric mesenchyme (MM) cells were transfected with the Amaxa Nucleofector 96-well Shuttle System (Lonza Group Ltd, Basel, Switzerland). Briefly, 1×10⁶ cells per transfection were resuspended in 20 µl of 96-well Nucleofector solutions. TOPflash luciferase plasmid (1 µg) and 0.1 µg pRL-TK-renilla plasmids (Promega, Madison, Wis., USA) were mixed with cell suspensions and transferred to the well of a 96-well Nucleocuvette module. Nucleofections were performed according to manufacturer's instructions using program DN-100.

MM cells were pre-treated with or without CT-HC-1 (10 µM) for 30 min, and then exposed to GSK3 inhibitor BIO (500 nM) or Wnt3a conditioned medium (50%) (Wnt3aCM as described in Willert et al., *Nature*, 423: 448-452 (2003)) for 24 hours. Cells were lysed and assayed for reporter activity using a Dual luciferase assay system (Promega) and a Monolight 3010 Luminometer (Pharmagen, San Diego, Calif., USA).

CT-HC-1 completely blocked BIO- and Wnt3aCM-induced transcription in cultured MM cells. Similar results were obtained with incubations for 1, 24, and 48 hours following the single addition of CT-HC-1.

Cells were also evaluated for levels of total β-catenin. In these studies, β-catenin was degraded within 3 hours of treatment with CT-HC-1. It was found that β-catenin levels had not recovered 24 hours after treatment with CT-HC-1. Since this suggested that the effect on transcriptional activation may be mediated through degradation of β-catenin, cells also were treated with proteasomal inhibitor MG132. β-catenin levels were stabilized even in CT-HC-1-treated cells, demonstrating that peptide activity is likely due to the accelerated degradation of its target.

To determine if the loss of β-catenin affects differentiation, MM cells were co-cultivated with inductor, embryonic spinal cord, and treated with CT-HC-1. In these cultures, tubule formation was unaffected. This finding was supported by semi-quantitative RT-PCR analysis of BIO-induced MM cells in which levels of epithelial markers Lim-1 and E-cadherin were unaltered with CT-HC-1 treatment. Furthermore, in cells exposed only to CT-HC-1 and not an inductive ligand, peptide treatment caused a decrease in Axin-2 expression, as expected, but it also enhanced expression of Lim-1 and E-cadherin. This observation is consistent with reports describing an antagonistic relationship between canonical and non-canonical Wnt mechanisms (see, e.g., Park et al., *Development*, 132: 2533-2539 (2007); and Schmidt-Ott et al., *Development*, 132: 3177-3190 (2007).

EXAMPLE 4

This example further illustrates the use of the inventive peptides and peptidomimetics to inhibit cell growth.

To identify a mouse model for preclinical development of compounds, mouse cell lines were tested for (1) growth inhibition by the compounds and (2) the levels of constitutive Wnt signaling TCF-reporter activity using transfection of cell with TCF/LEF-responsive firefly luciferase construct. The data further confirmed that sensitivity to compounds correlated well with the levels of canonical Wnt signaling.

Based on the data, mouse breast cancer cell line 4T1 was selected for in vivo testing. The cell line showed 5-fold increase in luciferase levels upon transfection, which is comparable with human colon cancer cell line HCT116 (10-fold increase) that has a deletion in the beta-catenin gene leading to its overexpression.

Further optimization and testing of inhibitors was performed using this cell line. Table 5 presents toxicity data for select inhibitors for 4T1 cells and human colon cancer cell line SW-480, wherein $GI_{50}$ is the concentration providing 50% growth inhibition and TGI is the total growth inhibition.

Previously, Western blot analysis of beta-catenin protein levels along with the use of proteosome inhibitors suggested that the inventive peptides and peptidomimetics cause beta-catenin degradation through the proteosomal pathway.

Using a cell line that contains GFP-CTNNB1 in its genome, reduction of beta-catenin levels using the inventive peptides and peptidomimetics was confirmed. Microscopy studies demonstrated drastic changes in beta-catenin localization and levels following administration of the inventive peptides and peptidomimetics. Colocalization studies with organelle markers revealed trafficking of β-catenin from

TABLE 5

| Compound | Structure | SEQ ID NO | SW480 cells $GI_{50}$ (nm) | SW480 cells TGI | 4T1 cells $GI_{50}$ (nm) | 4T1 cells TGI |
|---|---|---|---|---|---|---|
| CT-HC-1 | Pal-ε-KYKKRLSVELTSSLFR | 28 | 0.2 | 5 | 3.5 | >5 |
| CT-HC-3 | Pal-ε-KYKKRLSVQLTSSLFR | 32 | 0.4 | 0.5 | 4.5 | >5 |
| CT-HC-2 | Pal-NKPQDYKKRLSVELTSSLFR | 31 | >5 | >5 | >5 | >5 |
| CT-HC-12 | Pal-YKKRLSVELTSSLFR | 30 | 2 | >5 | 4 | >5 |
| CT-HC-16 | Pal-YKKRLSVELTSSLFRTEPMAW | 43 | >5 | >5 | 1 | >5 |
| CT-HC-13 | Pal-Aib-YKKRLSVELTSSLFR | 44 | In testing | In testing | >5 | >5 |
| CT-HC-19 | Pal-Aib-YKKRLSVQLTSSLFR | 45 | In testing | In testing | 0.4 | >5 |
| CT-HC-8 | Doa-YKKRLSVELTSSLFR | 33 | 0.15 | 0.4 | >5 | >5 |
| CT-HC-9 | Ac-YKKRLS+ELT+SLFR (Stapled) | 34 | >5 | >5 | >5 | >5 |
| CT-HC-5 | Pal-TRFLSSTLEVSLRKK-NH$_2$ (All-D) | 36 | 1.5 | 2.5 | 3.2 | >5 |
| CT-HC-15 | Pal-TRFLSSTLQVSLRKK-NH$_2$ (All-D) | 46 | In testing | In testing | 2.0 | 3.6 |
| CT-HC-20 | Pal-RFLSSTLQVSLRKK-NH$_2$ (All-D) | 47 | In testing | In testing | 3.6 | >5 |
| CT-HC-22 | Cap-TRFLSSTLQVSLRKK-NH$_2$ (All-D) | 48 | — | — | 4.6 | >5 |
| CT-HC-23 | Lau-TRFLSSTLQVSLRKK-NH$_2$ (All-D) | 49 | — | — | 1.8 | 3.5 |
| CT-HC-10 | Pal-TRFLSSTLEVSLRKKY-NH$_2$ (All-D) | 37 | 1.5 | 2.2 | 0.6 | 2 |
| CT-HC-11 | Pal-Aib-TRFLSSTLQVSLRKK-NH$_2$ (All-D) | 38 | In testing | In testing | 1.1 | 3 |

Doa = 2-dodecyl-alanine
Aib = amino-isobutyric acid
+ = 2-(4'-pentenyl)alanine (which is involved in hydrocarbon stapling of the peptide)
Ac = acetyl
Cap = capric acid
Lau = lauric acid Based on these experiments, CT-HC-5, CT-HC-11, CT-HC-15, and CT-HC-23 were considered to be the most potent derivatives. All are constructed from All-D amino acids and thus are likely to be sufficiently stable in circulation.

The activity of compounds in inhibiting colony formation by 4T1 cells was also investigated, which test provides a prediction for compound's potency in vivo. In particular, inhibition of colony formation by 4T1 mouse breast cancer cells was investigated using CT-HC-5 and a control inactive peptide (EpCam1) at concentrations of 5 μM and 10 μM. CT-HC-5, but not the control, inhibited colony formation by 4T1 mouse breast cancer cells (most significantly at the higher tested concentration (10 μM).

EXAMPLE 5

The example demonstrates the mechanism of action of the inventive peptides and peptidomimetics.

membranes to lysosomes upon treatment with the inventive peptides and peptidomimetics.

In addition, Western blot analysis of cell extracts immunoprecipitated with anti-beta-catenin antibodies or anti-GFP antibodies (in the case of GFP-catenin fusions) have demonstrated induction of β-catenin ubiquitination by treatment with the inventive peptides and peptidomimetics.

Furthermore, microscale thermophoresis of GFP-tagged beta-catenin demonstrated direct interaction of the inventive peptides and peptidomimetics (CT-HC-5) with the protein. Briefly, beta-catenin was overexpressed as a GFP-fusion in HEK293 cells. The cells were lysed with ultrasound, and the resulting lysate was mixed with increasing concentrations of CT-HC-5 in the presence of membrane-mimicking bicelles. Thermophoretic mobility was measured in standard capillaries on Monolith NT.115 (NanoTemper Technologies). The curve was fitted using Hill method and produced $K_D$=2.7±0.2 μM.

EXAMPLE 6

This example demonstrates in vivo administration of the inventive peptides and peptidomimetics.

CT-HC-11 has been tested in 4T1 breast cancer mouse model at two doses: 10 and 2 mg/kg injected subcutaneously three times a week alone or in combination with weekly gemcitabine (75 mg/kg). Although testing is ongoing, after three drug injections, a 2 mg/kg dose of CT-HC-11 administered alone showed significant reduction in tumor volume.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A peptide or peptidomimetic comprising the amino acid sequence KKRLSVXLTSSLFR (SEQ ID NO: 1) or the inverse thereof, wherein the peptide or peptidomimetic comprises about 50 or fewer amino acids and inhibits the Wnt pathway.

2. The peptide or peptidomimetic of claim 1, wherein X is an acidic or uncharged polar amino acid.

3. The peptide or peptidomimetic of claim 1, wherein X is a glutamic acid or glutamine.

4. The peptide or peptidomimetic of claim 1 comprising about 25 or fewer amino acids.

5. The peptide or peptidomimetic of claim 1 comprising the amino acid sequence

KKRLSVXLTSSLFR (SEQ ID NO: 1)

$X_3$KKRLSVXLTSSLFR (SEQ ID NO: 2)

$X_3$KKRLSVXLTSSLFR$X_4$ (SEQ ID NO: 3)

KKRLSVXLTSSLFR$X_4$ (SEQ ID NO: 4)

KKRLSVXLTSSLFR$X_4X_5$ (SEQ ID NO: 5)

$X_3$KKRLSVXLTSSLFR$X_4X_5$ (SEQ ID NO: 6)

KKRLSVELTSSLFR (SEQ ID NO: 7)

$X_3$KKRLSVELTSSLFR (SEQ ID NO: 8)

$X_3$KKRLSVELTSSLFR$X_4$ (SEQ ID NO: 9)

KKRLSVELTSSLFR$X_4$ (SEQ ID NO: 10)

KKRLSVELTSSLFR$X_4X_5$ (SEQ ID NO: 11)

$X_3$KKRLSVELTSSLFR$X_4X_5$ (SEQ ID NO: 12)

KKRLSVQLTSSLFR (SEQ ID NO: 13)

$X_3$KKRLSVQLTSSLFR (SEQ ID NO: 14)

```
                                                  (SEQ ID NO: 15)
X3KKRLSVQLTSSLFRX4

(SEQ ID NO: 16)
KKRLSVQLTSSLFRX5

(SEQ ID NO: 17)
KKRLSVQLTSSLFRX4X5

(SEQ ID NO: 18)
X3KKRLSVQLTSSLFRX4X5

(SEQ ID NO: 40)
X1X2X3YKKRLSVELTSSLFR
``` or the inverse of any such sequences, wherein $X_1$ is a nonpolar and uncharged amino acid and $X_2$, $X_3$, $X_4$, and $X_5$ are polar amino acids.

6. The peptide or peptidomimetic of claim 1 comprising one of SEQ ID NOs: 28-33 and 35-39.

7. A peptide or peptidomimetic comprising at least eight contiguous amino acids of helix C of β-catenin (SEQ ID NO: 41), or inverse thereof, wherein the peptide or peptidomimetic comprises a total of about 50 or fewer amino acids.

8. The peptide or peptidomimetic of claim 1, wherein the peptide or peptidomimetic comprises one or more D-amino acids.

9. The peptide or peptidomimetic of claim 1 further comprising a cell-penetrating motif.

10. The peptide or peptidomimetic of claim 1 further comprising a protein transduction domain or fatty acid, optionally attached to the peptide or peptidomimetic via a linker sequence.

11. The peptide or peptidomimetic of claim 1, wherein the peptide or peptidomimetic comprises a terminal palmitoyl group.

12. The peptide or peptidomimetic of claim 11, wherein the peptide or peptidomimetic comprises an N-terminal palmitoyl residue or an N-terminal palmitoyl-ε-lysine residue.

13. A pharmaceutical composition comprising the peptide or peptidomimetic of claim 1, and a pharmaceutically acceptable carrier.

14. A method of inhibiting the Wnt pathway in a cell comprising introducing a peptide or peptidomimetic of claim 1 into the cell, whereby the Wnt pathway is inhibited.

15. The method of claim 14, wherein inhibiting the Wnt pathway comprises inhibiting β-catenin overexpression, up-regulation, or overabundance.

16. The method of claim 14, wherein the peptide or peptidomimetic is introduced into the cell by contacting the cell with the peptide or peptidomimetic.

17. A method for inhibiting the growth or proliferation of a cancer cell comprising administering a peptide or peptidomimetic of claim 1 to the cancer cell, whereupon the growth or proliferation of the cancer cell is inhibited.

18. The method of claim 14, wherein the cell is in a host.

19. The method of claim 18, wherein the host is a mammal.

20. A method of treating a disease mediated by the Wnt pathway in a host comprising administering to the host a peptide or peptidomimetic of claim 1, whereby the disease is treated.

21. The method of claim 20, wherein the disease is cancer.

22. The peptide or peptidomimetic of claim 1, wherein the peptide or peptidomimetic comprises the inverse of the amino acid sequence of SEQ ID NO: 1.

23. A peptidomimetic comprising the amino acid sequence KKRLSVXLTSSLFR (SEQ ID NO: 1) or the inverse thereof, wherein the peptidomimetic comprises about 50 or fewer amino acids and inhibits the Wnt pathway.

* * * * *